DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 27, 1973

908 O.G. 788

T908,004

PREPARATION OF THIOLHYDROXAMATE CARBAMATES

Earl W. Cummins, Oak Lane Manor, 2410 Shellpot Drive, Wilmington, Del. 19803

Continuation of application Ser. No. 872,725, Oct. 30, 1969. This application Oct. 7, 1971, Ser. No. 187,549

Int. Cl. C07c *119/00*

U.S. Cl. 260—453 R

No Drawing. 15 Pages Specification

In the preparation of thiolhydroxamate carbamates of the formula:

(1)

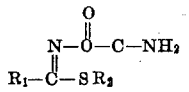

wherein $R_1$ is methyl, ethyl, methoxymethyl or (methylthio) methyl; and $R_2$ is methyl, ethyl or propyl;

by reaction of a thiolhydroxamate ester of the formula:

(2)

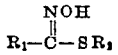

with isocyanic acid in an aqueous medium optionally containing up to 50% of a nonreactive organic liquid, at a temperature between the freezing point and boiling point of the reaction mass (usually between −15° C. and 80° C.), improved yields are obtained by maintaining the pH between 1.5 and 5.0, preferably between 2.5 and 4.5, most preferably between 3.5 and 4.0. The isocyanic acid can be generated in situ by concurrent addition of an alkali metal cyanate such as sodium cyanate and a mineral acid such as $H_2SO_4$ to the reaction mass.